(12) United States Patent
Weichselbaum et al.

(10) Patent No.: US 11,013,856 B2
(45) Date of Patent: May 25, 2021

(54) VISCOELASTIC SPRING SYRINGE

(71) Applicants: Amnon Weichselbaum, Haifa (IL);
Yechiel Lisner, Raanana (IL)

(72) Inventors: Amnon Weichselbaum, Haifa (IL);
Yechiel Lisner, Raanana (IL)

( * ) Notice: Subject to any disclaimer, the term of this patent is extended or adjusted under 35 U.S.C. 154(b) by 0 days.

(21) Appl. No.: 16/068,988

(22) PCT Filed: Jan. 11, 2017

(86) PCT No.: PCT/IB2017/050134
§ 371 (c)(1),
(2) Date: Jul. 10, 2018

(87) PCT Pub. No.: WO2017/122134
PCT Pub. Date: Jul. 20, 2017

(65) Prior Publication Data
US 2019/0022307 A1      Jan. 24, 2019

Related U.S. Application Data

(60) Provisional application No. 62/278,521, filed on Jan. 14, 2016.

(51) Int. Cl.
*A61M 5/145*     (2006.01)
*A61M 25/10*     (2013.01)

(52) U.S. Cl.
CPC ...... *A61M 5/14526* (2013.01); *A61M 5/1454* (2013.01); *A61M 25/10* (2013.01); *A61M 2005/14506* (2013.01); *A61M 2205/0216* (2013.01); *A61M 2209/088* (2013.01)

(58) Field of Classification Search
CPC .......... A61M 5/145–5/155; A61M 2005/2086; A61M 2005/3143; A61M 5/20–2005/202; A61M 5/2033; A61M 5/14276–2005/14284; A61M 2005/3115; G01F 11/021; G01F 11/027
See application file for complete search history.

(56) References Cited

U.S. PATENT DOCUMENTS

| | | | | |
|---|---|---|---|---|
| 2,605,099 A | * | 7/1952 | Brown | F16F 3/12 267/33 |
| 4,278,726 A | * | 7/1981 | Wieme | A63C 5/075 428/300.7 |
| 4,772,263 A | * | 9/1988 | Dorman | A61M 5/14276 128/DIG. 12 |
| 5,178,609 A | | 1/1993 | Ishikawa | |

(Continued)

FOREIGN PATENT DOCUMENTS

JP         2008291867         * 12/2008

OTHER PUBLICATIONS

Solvay, Torlon PAI Processing Guide, 2015,www.solvay.com,p. 11. (Year: 2015).*

(Continued)

*Primary Examiner* — Phillip A Gray
(74) *Attorney, Agent, or Firm* — Dekel Patent Ltd.; David Klein

(57) ABSTRACT

A syringe includes a plunger and a spring embedded in a viscoelastic material. Expansion of the spring and the viscoelastic material applies a force on the plunger to move the plunger distally in the syringe.

5 Claims, 1 Drawing Sheet

(56) References Cited

U.S. PATENT DOCUMENTS

| | | | | |
|---|---|---|---|---|
| 5,318,539 A * | 6/1994 | O'Neil | ............... | A61M 5/1409 |
| | | | | 604/118 |
| 5,531,696 A | 7/1996 | Menes | | |
| 5,944,693 A | 8/1999 | Jacobs | | |
| 2008/0103580 A1 * | 5/2008 | Gerber | ............... | A61N 1/0534 |
| | | | | 607/149 |
| 2008/0319393 A1 | 12/2008 | Elder | | |
| 2011/0257596 A1 * | 10/2011 | Gaudet | ............... | A61M 5/1452 |
| | | | | 604/154 |

OTHER PUBLICATIONS

PCT Search and Written Opinion PCT/IB2017/050134, dated May 18, 2017.

* cited by examiner

VISCOELASTIC SPRING SYRINGE

FIELD OF THE INVENTION

The present invention relates generally to syringes, and particularly to a syringe whose plunger is moved by the force of a spring embedded in a viscoelastic material, such as a polymer-matrix composite.

BACKGROUND OF THE INVENTION

Syringes for dispensing medical materials, such as used with hypodermic needles and the like, typically have a plunger that slides in a cylindrical housing. The plunger may be pushed by hand to force material out through the needle tip.

In other applications, the syringe may form part of a pumping system. Conventional syringe pumps are typically employed with either a syringe or a vial and plunger system for administering a liquid to a patient. In such conventional systems, a syringe or vial of the liquid is oriented vertically in a fixed position on the syringe pump. The bottom of the syringe or vial defines a discharge port connected to a flexible, hollow tubing which extends to the patient. The plunger or piston of the apparatus is engaged with the moving pusher plate or drive member of the syringe pump and is driven downwardly into the syringe body or vial to force the liquid agent from the syringe body or vial through the tubing and into the patient.

In another example, U.S. Pat. No. 8,088,105 describes a syringe pump with a syringe including a plunger that slides in a body which has a discharge port. A driving mechanism is coupled to the syringe, including a cylinder in which a piston mounted on a shaft slides. A biasing device applies an urging force on the piston to drive the piston distally in the cylinder. A safety catch initially prevents the biasing device from moving the piston. The safety catch is removable to permit the biasing device to move the piston. The system uses a mechanical spring mechanism connected to a dashpot in order to produce the linear displacement of the syringe.

SUMMARY OF THE INVENTION

The present invention seeks to provide a syringe whose plunger is moved by the force of a spring embedded in a viscoelastic material, such as a polymer-matrix composite, as is described more in detail hereinbelow. In one application, the syringe may function for slow release of drugs or antibiotics to wounds and burns. The system of the present invention provides several advantages: the spring embedded in the viscoelastic material provides significant savings in space, cost and ease of manufacture.

There is provided in accordance with an embodiment of the invention a syringe including a plunger and a spring embedded in a viscoelastic material, wherein expansion of the spring and the viscoelastic material applies a force on the plunger to move the plunger distally in the syringe.

In accordance with an embodiment of the invention the viscoelastic material includes a polymer-matrix composite (PMC), which includes elastic fibers bound together by an organic polymer matrix, the spring being made of the fibers. The force of the spring and the viscoelastic material may cause a uniform and linear displacement of the plunger.

In accordance with an embodiment of the invention the syringe is connected to a catheter that transfers the liquid material to the treated area.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
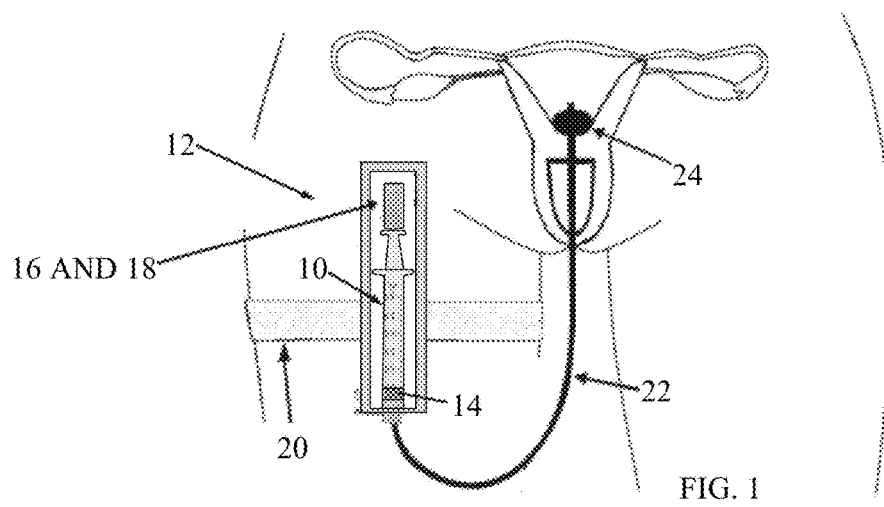
FIG. 1 is a simplified pictorial illustration of a syringe being used in a syringe pump system for medical treatment, constructed and operative in accordance with an embodiment of the present invention.
Figure 2:
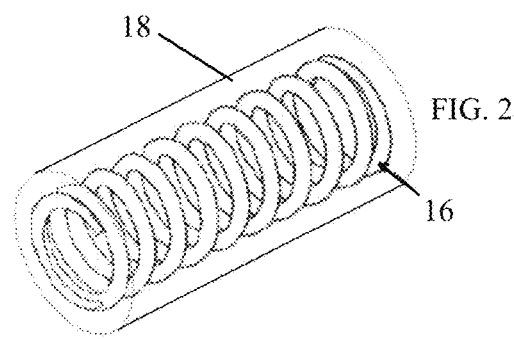
FIG. 2 is a simplified pictorial illustration of a spring of the syringe embedded in a viscoelastic material, such as a polymer-matrix composite, in accordance with an embodiment of the present invention.

Reference is now made to FIG. 1, which illustrates a syringe 10 being used in a syringe pump system 12, constructed and operative in accordance with an embodiment of the present invention. As will be described further below, the syringe 10 has a plunger 14 which is urged by the force of a spring 16 (FIG. 2) embedded in a viscoelastic material 18 (FIG. 2).

The syringe pump system 12 is only one application for the syringe and the invention is not limited to this application. The medical liquid may be delivered via a catheter 22 to the treated area. The syringe 10 may be strapped to the patient's body (leg or arm) with a strap 20. The syringe 10 is at least partially filled with a medical fluid, which is delivered via catheter 22 to the treated area. An optional inflatable anchoring balloon 24 may be used to anchor the catheter 22 inside a lumen of an organ such as urethra, intestine, uterus or others).

The actuation mechanism of the syringe 10, that is, the mechanism that urges the plunger 14, is the spring 16 disposed in the viscoelastic material 18, which may be a pre-compressed viscoelastic material. The combination of the spring 16 and viscoelastic material 18 may provide a uniform and linear displacement against the resistance of the medical fluid flow and the syringe's internal friction (static and dynamic), and may provide a final, rapid ejection of a trapped air bubble in the syringe, in order to clear the catheter of medical fluid.

The viscoelastic material 18 may be a light weight polymer-matrix composite (PMC), which includes a variety of short or continuous elastic fibers bound together by an organic polymer matrix. The fiber reinforcement in the PMC may deform in response to the mechanical force of spring 16. The matrix bonds the elastic fibers together and transfers loads between them. The PMC may exhibit anisotropic deformation along the direction of the elastic component's orientation. The fibers serve as spring 16 embedded in the matrix of viscoelastic material 18.

Figure 3:
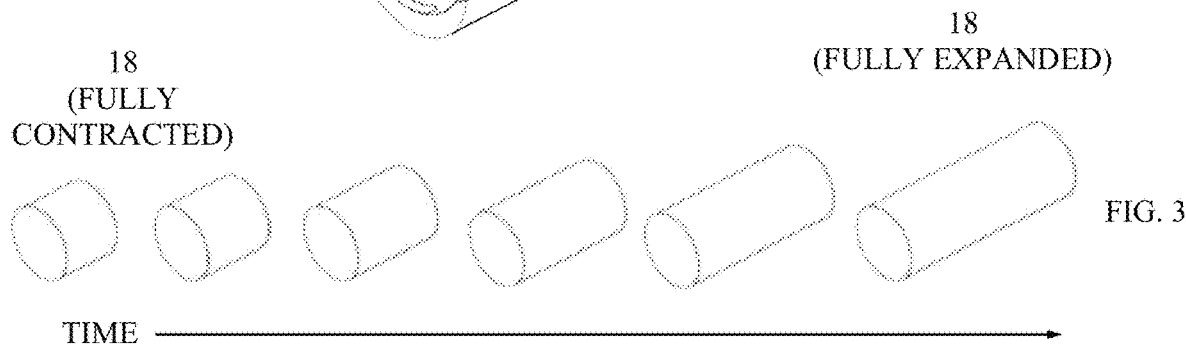
FIG. 3 is a simplified pictorial illustration of gradual expansion of the spring embedded in the viscoelastic material over time.
Figure 4:
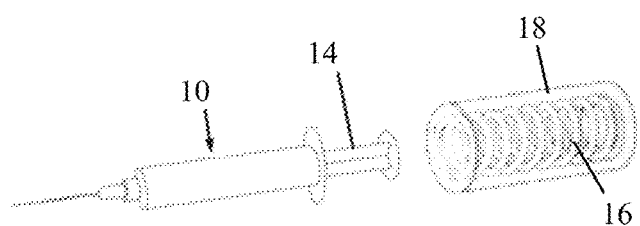
FIG. 4 is a simplified pictorial illustration of the spring embedded in the viscoelastic material about to be assembled with the syringe.

The viscoelastic polymer-based actuation system may replace the spring-loaded, fluid-based system of the prior art. As seen in FIG. 2, the polymer-matrix composite includes the pre-compressed spring 16 embedded within viscoelastic polymer 18. Upon the release of the initial compressive confinement (such as by releasing a safety catch), the pre-compressed spring 16 begins to deform immediately. As spring 16 begins to extend, the viscoelastic polymer matrix 18 entraps it and confines its movement, thereby slowing the rate of extension. The dissipative effect of the confining viscoelastic polymer 18 as it deforms, mitigates the displacement of spring 16. The gradual expansion of the viscoelastic polymer 18 is shown in FIG. 3.

What is claimed is:

1. A method for dispensing a medical fluid comprising:
   providing a syringe comprising a plunger and a spring comprising coils, said coils and spaces between said coils being embedded in a viscoelastic material, wherein expansion of said spring and said viscoelastic material applies a force on said plunger to move said plunger distally in said syringe;
   wherein said syringe is at least partially filled with a medical fluid and said spring is pre-compressed in said viscoelastic material before said plunger moves distally in said syringe, and
   releasing an initial compressive confinement of said pre-compressed spring so that said spring begins to extend immediately, and then as said spring extends in said viscoelastic material, said viscoelastic material entraps said spring and confines movement of said spring, thereby slowing a rate of extension of said spring, wherein said spring urges said plunger to dispense the medical fluid from said syringe.

2. The method according to claim 1, wherein the force of said spring and said viscoelastic material causes a uniform and linear displacement of said plunger against resistance of flow of the medical fluid and static and dynamic friction in said syringe.

3. The method according to claim 2, wherein said syringe is connected to a catheter.

4. The method according to claim 3, wherein said force provides a final, rapid ejection of a trapped air bubble in said syringe in order to clear said catheter of any remainder of the medical fluid.

5. The method according to claim 1, wherein said viscoelastic material undergoes anisotropic deformation.

\* \* \* \* \*